United States Patent
Raynaud et al.

(10) Patent No.: US 11,341,634 B2
(45) Date of Patent: May 24, 2022

(54) FETAL ULTRASOUND IMAGE PROCESSING

(71) Applicant: KONINKLIJKE PHILIPS N.V., Eindhoven (NL)

(72) Inventors: Caroline Denise Francoise Raynaud, Paris (FR); Laurence Rouet, Paris (FR); Cybèle Ciofolo-Veit, Meudon (FR); Thierry Lefevre, Suresnes (FR); David Nigel Roundhill, Woodinville, WA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 177 days.

(21) Appl. No.: 16/630,919

(22) PCT Filed: Jul. 12, 2018

(86) PCT No.: PCT/EP2018/068909
§ 371 (c)(1),
(2) Date: Jan. 14, 2020

(87) PCT Pub. No.: WO2019/016064
PCT Pub. Date: Jan. 24, 2019

(65) Prior Publication Data
US 2020/0234435 A1  Jul. 23, 2020

Related U.S. Application Data

(60) Provisional application No. 62/533,702, filed on Jul. 18, 2017.

(30) Foreign Application Priority Data

Jul. 27, 2017   (EP) .................................. 17183432

(51) Int. Cl.
*G06K 9/00* (2022.01)
*G06T 7/00* (2017.01)
(Continued)

(52) U.S. Cl.
CPC .......... *G06T 7/0012* (2013.01); *A61B 8/0866* (2013.01); *A61B 8/483* (2013.01);
(Continued)

(58) Field of Classification Search
CPC ..................................................... G06T 7/0012
See application file for complete search history.

(56) References Cited

U.S. PATENT DOCUMENTS

2009/0093717 A1   4/2009 Carneiro et al.
2010/0099987 A1   4/2010 Sasaki et al.
(Continued)

FOREIGN PATENT DOCUMENTS

WO    2006104959 A2   10/2006
WO    2017009812 A1   1/2017

OTHER PUBLICATIONS

Gauriau, et al., "Multi-organ Localization Combining Global-to-Local Regression and Confidence Maps", Network and Parallell Computing, Sep. 14, 2014, pp. 337-344.
(Continued)

*Primary Examiner* — Oneal R Mistry

(57) ABSTRACT

A computer implemented method is provided for processing a 3D fetal ultrasound image. A 3D fetal ultrasound image is obtained (either acquired or received from memory), and the spine is detected within the image. This enables a first reference axis to be defined. A second reference axis is defined perpendicular to the first reference axis, and the 3D fetal ultrasound image is updated (e.g. rotated in 3D space) using the first and second reference axes and an up/down (elevation) orientation detection. This provides a normalization of the orientation of the image, so that a machine learning approach is better able to identify landmarks within new images.

14 Claims, 7 Drawing Sheets

(51) Int. Cl.
*G06T 7/73* (2017.01)
*A61B 8/08* (2006.01)
(52) U.S. Cl.
CPC .............. *A61B 8/5223* (2013.01); *G06T 7/73* (2017.01); *G06T 2207/10136* (2013.01); *G06T 2207/20081* (2013.01); *G06T 2207/30012* (2013.01); *G06T 2207/30044* (2013.01)

(56) References Cited

U.S. PATENT DOCUMENTS

| | | | | |
|---|---|---|---|---|
| 2011/0125016 | A1* | 5/2011 | Lazebnik | A61B 8/0866 600/443 |
| 2014/0378837 | A1* | 12/2014 | Fujiwara | A61B 8/463 600/443 |
| 2016/0081663 | A1* | 3/2016 | Chen | A61B 8/0866 600/425 |
| 2016/0242742 | A1 | 8/2016 | Gratacos Solsona et al. | |
| 2018/0275258 | A1* | 9/2018 | Pintoffl | G01S 7/52046 |
| 2020/0205772 | A1* | 7/2020 | Zou | A61B 8/523 |

OTHER PUBLICATIONS

Nie, et al., "Automatic Detection of Standard Sagittal Plane in the First Trimester of Pregnancy Using 3-D Ultrasound Data", Ultrasound in Medicine and Biology, vol. 43, No. 1, Jan. 1, 2016, pp. 286-300.

Yang, et al., "Standard Plane Localization in Ultrasound by Radial Component", 2014 IEEE 11th International Symposium on Biomedical Imaging (ISBI), IEEE, Apr. 29, 2014, pp. 1180-1183.

Chen, et al., "Ultrasound Standard Plane Detection Using a Composite Neural Network Framework", IEEE Transactions on Cybernetics, vol. 47, No. 6, Jun. 2017, pp. 1576-1586.

Chen, et al., "Fetal Abdominal Standard Plane Localization through Representation Learning with Knowledge Transfer", Network and Parallel Computing, Sep. 14, 2014, pp. 125-132.

Yu, et al., "Fetal Facial Standard Plance Recognition via Very Deep Convolutional Networks", 2016 38th Annual International Conference of the IEEE Engineering in Medicine and Biology Society, IEEE, Aug. 16, 2016, pp. 627-630.

Raynaud, et al., "Multi-organ Detection in 3D Fetal Ultrasound with Machine Learning", Sep. 9, 2017, Network and Parallel Computing, pp. 62-72.

International Search Report and Written Opinion for International Application No. PCT/EP2018/068909, filed Jul. 12, 2018, 15 pages.

Yaqub, et al., "Plane Localization in 3-D Fetal Neurosonography for Longitudinal Analysis of the Developing Brain", In IEEE Journal of Biomedical and Health Informatics, vol. 00, No. 00, May 20, 2015 (e-publication ahead of print), pp. 1-9.

Chen, et al., "Automatic Fetal Ultrasound Standard Plane Detection Using Knowledge Transferred Recurrent Neural Networks", In MICCAI 2015, Part I, LNCS 9349, Springer 2015, pp. 507-514.

Ni, et al., "Stardard Plane Localization in Ultrasound by Radial Component Model and Selective Search", Ultrasound in Medicine and Biology, vol. 40, No. 11, pp. 2728-2742.

Papageorghiou, et al., "International standards for fetal growth based on serial ultrasound measurements: the Fetal Growth Longitudinal Study of the INTERGROWTH-21st Project", The Lancet, Sep. 6, 2014, vol. 384, pp. 869-879.

* cited by examiner

FETAL ULTRASOUND IMAGE PROCESSING

RELATED APPLICATIONS

This application is the U.S. National Phase application under 35 U.S.C. § 371 of International Application No. PCT/EP2018/068909, filed on Jul. 12, 2018, which claims priority to and the benefit of Provisional Application No. 62/533,702, filed Jul. 18, 2017 and of European Application No. 17183432.8, filed Jul. 27, 2017. These applications are hereby incorporated by reference herein.

FIELD OF THE INVENTION

This invention relates to the processing of fetal ultrasound images.

BACKGROUND OF THE INVENTION

In a clinical setting, 2D ultrasound (US) is the preferred scanning protocol for biometry measurements, growth monitoring and anatomy assessment during pregnancy. Obtaining reproducible and accurate values requires strict guidelines to be followed, especially regarding the selection of the standard 2D viewing planes which are used to search for abnormalities or perform biometry measurements such as head and abdomen circumference or femur length. This task can be very difficult because of multiple factors, such as the mother morphology, the unknown and highly variable orientation of the fetus as well as well-known US artefacts, in particular the shadowing effect.

3D US is a more recent imaging technique that has the potential to overcome some of the above mentioned difficulties. In particular, the acquisition of a single 3D volume makes it possible to select the required viewing planes. In addition, the clinicians can perform offline reading and, if necessary, adjust the position of the extracted planes (called "clinical planes") prior to standard measurements.

It would be desirable to process 3D US volumes automatically to enable extraction of the targeted clinical planes. However this task is challenging due to the high variability of the fetus orientation at the acquisition time. Various strategies have been proposed for automatic viewing plane extraction in 2D. Views of interest can be selected from 2D US sequences by classifying the content of each frame to determine if it corresponds to a standard plane using a radial component model or a pre-trained recurrent neural network.

Document US 2010/099,987 A1 describes an ultrasonic image acquisition and diagnosis display technique in which the spine of a fetus included in a 3D volume scan is used as a landmark for recognizing the position of the heart in the chest of the fetus with high accuracy.

Another 2D approach consists in fitting geometrical templates built at multiple resolutions and orientations in order to label the anatomical content.

There remains a need for a more reliable automated approach for extracting information of interest from a 3D fetal US image.

SUMMARY OF THE INVENTION

According to examples in accordance with an aspect of the invention, there is provided a computer implemented method for processing a 3D fetal ultrasound image, the method comprising:
  obtaining a 3D fetal ultrasound image;
  detecting the spine within the image;
  determining a first reference axis based on the spine orientation and location within the image;
  determining a second reference axis, perpendicular to the first reference axis, based on the fetal torso orientation with respect to the detected spine; and
  updating the 3D fetal ultrasound image using the first and second reference axes.

This method enables alignment of a 3D volume image using two reference axes, in order to provide a normalized representation which removes variation resulting from different fetus orientations. A first reference axis is based on the spine, and it may be the direction of the spine in the middle of the spine, or it may be the direction of the vector connecting identified end points of the spine, for example. The spine is a well-defined, unique structure within the fetus that will be readily recognizable to the ultrasound system, particularly when using image recognition techniques.

The second reference axis enables volume rotation about the spine (i.e. about the first reference axis), so that a 3D orientation of the fetus is identified. The updated image may be a rotated version of the image, or it may be the image with additional data annotations identifying the reference axes.

The method may be implemented in real time, so that the 3D ultrasound image is obtained by an ultrasound scan as part of the method. Alternatively, the method may be applied to a previously captured image.

By providing a normalized volume orientation, identification of landmark points (such as organs) within the image is made possible by an automated machine learning approach. The method may for example be used to process samples of a training database to provide a machine learning operation, and then the machine learned algorithm may be used to process an unseen captured image (i.e. one not included already processed to create the training database) to provide automated identification.

The invention may be considered to provide an image filtering or normalization process which can be applied before applying machine learning approaches in order to perform automatic extraction of the clinical planes of interest.

The determining of the second reference axis comprises:
  extracting a set of planes, each orthogonal to the first reference axis or locally orthogonal to the spine;
  detecting an elliptical or circular form of the abdomen or thorax of the fetus in each plane; and
  determining the second reference axis based on an orientation vector in each plane between the spine and the center of the elliptical form.

The spine is at one edge of the abdomen/thorax, so the vector between the spine and the center of the ellipse (or circle) represents a rotational orientation. In this way, it is possible to normalize the orientation of the 3D volume images based on the torso/abdominal shape of the fetus. As the torso/abdomen is the largest portion of the fetus, it is easily measurable, thereby increasing the accuracy of the alignment.

The elliptical or circular form is for example obtained by performing a Hankel transform on the plane.

The generating of the second reference axis may comprise:
  projecting the orientation vectors on a central plane located at the middle of the spine; taking an average of the projected orientation vectors; and
  using the average of the projected orientation vectors to form the second reference axis.

By generating the transverse axis based on an average of the projected orientation values, a second reference axis is obtained which is reliably consistent between different images.

Taking an average may comprise calculating a weighted average, with greater weighting in the middle of the spine than at the ends of the spine.

The method may further comprise:

determining a head/toe orientation of the 3D fetal ultrasound image; and updating the 3D fetal ultrasound image using the head/toe orientation.

This involves determining the orientation of the 3D images with respect to the up-down fetus position, i.e. to determine at which end of the spine is the head at which end is the buttocks (and then the legs down to the toes). This may be considered to be an elevation orientation. The updating may again comprise an image manipulation or annotation of the image with an up/down indication.

The method may further comprise:

performing intensity normalization on the 3D fetal ultrasound image; and/or scaling the 3D fetal ultrasound image based on a fetal gestation age.

In this way, the scale variability between 3D fetal ultrasound images due to gestation age is reduced, and/or the intensity variation due to varying image acquisition gains and imaging conditions may be reduced. The scaling and intensity normalization may take place before or after the reference axis determination and re-orientation.

The detecting of the spine within the 3D fetal ultrasound image for example comprises:

analyzing the image with a morphological filter adapted to detect elongated bright structures;

analyzing the image with a deep learning-based vertebrae detector; and obtaining a spine mask based on the responses from the morphological filter and from the deep learning-based vertebrae detector.

The spine mask is preferably a binary mask.

In this way, the detection of the spine takes advantages of the strengths of both methods, so that the position of the spine within the 3D fetal ultrasound image can be more robustly determined.

The invention also provides a method of generating a training database based on 3D fetal ultrasound images and generating an algorithm, comprising:

receiving a training set of 3D fetal ultrasound images;

receiving identification of landmarks within each 3D fetal ultrasound image of the training set;

processing each 3D fetal ultrasound image of the training set using the method as defined above;

orienting each 3D fetal ultrasound image of the training set using the respective first and second reference axes and head/toe orientation; and using machine learning to the oriented training set to provide an algorithm which can determine the location of landmarks for a 3D fetal ultrasound image without corresponding identification of landmarks.

The landmark identifications in the received training set are for example manually provided by a clinician. These provide the information for a machine learning algorithm to be able to identify the landmarks in a new image. The landmarks are for example organs, such as the heart, bladder, kidneys and umbilical insertion.

During the training database generation, the method may comprise determining the head/toe orientation of the fetus by:

extracting a plane of interest defined by the first and second reference axes;

randomly sampling patches, of a determined patch size, of the extracted plane of interest; and generating a classifier based on the patches, wherein the classifier indicates the head/toe orientation of the fetus.

By generating a classifier for a 3D volume image based on randomly sampled patches of an extracted plane, it is possible to efficiently represent the orientation of the 3D volume image, for example as a binary indicator. The patch size is for example based on a fetal gestation age and a resolution of the 3D fetal ultrasound image.

The invention also provides a method of identifying landmarks within a 3D fetal ultrasound image, comprising:

receiving a 3D fetal ultrasound image;

processing the 3D fetal ultrasound image using the method as defined above;

orienting the 3D fetal ultrasound image using the first and second reference axes; and analyzing the oriented 3D fetal ultrasound image with a machine learning algorithm derived from a training database which comprises landmark information, thereby to locate corresponding landmark information for the 3D fetal ultrasound image.

This method provides identification of landmarks using the previous machine learning from the testing database, so that the landmarks may be located in an automated way. The 3D orientation processing removes or reduces uncertainties resulting from unknown fetal positions.

The identified landmarks may then be used to control the generation of 2D image planes of interest, namely planes which pass through organs or other landmarks of interest, or are defined with respect to the position of such organs or other landmarks.

The training database used in this method is generated using the method as defined above.

The invention also provides a computer program and a controller for controlling the processing a 3D fetal ultrasound image, wherein the controller comprises instructions thereon that when executed cause the controller to implement the methods defined above.

The invention also provides an ultrasound system, the system comprising:

an ultrasonic probe, the ultrasonic probe comprising an array of transducer elements, wherein the ultrasonic probe is adapted to obtain a 3D fetal ultrasound image of a region of interest;

a controller as defined above; and a display device for displaying the aligned 3D fetal ultrasound image, wherein the controller is adapted to analyze the updated 3D fetal ultrasound image using a machine learning algorithm derived from a training database, thereby to derive landmark locations within the 3D fetal ultrasound image.

BRIEF DESCRIPTION OF THE DRAWINGS

Examples of the invention will now be described in detail with reference to the accompanying drawings, in which.

DETAILED DESCRIPTION OF THE EMBODIMENTS

The invention provides a computer implemented method for processing a 3D fetal ultrasound image. A 3D fetal ultrasound image is obtained (either acquired or received from memory), and the spine is detected within the image. This enables a first reference axis to be defined. A second reference axis is defined perpendicular to the first reference axis, and the 3D fetal ultrasound image is updated (e.g. rotated in 3D space) using the first and second reference axes and an up/down (elevation) orientation detection. This provides a normalization of the orientation of the image, so that a machine learning approach is better able to identify landmarks within new images.

Figure 1:
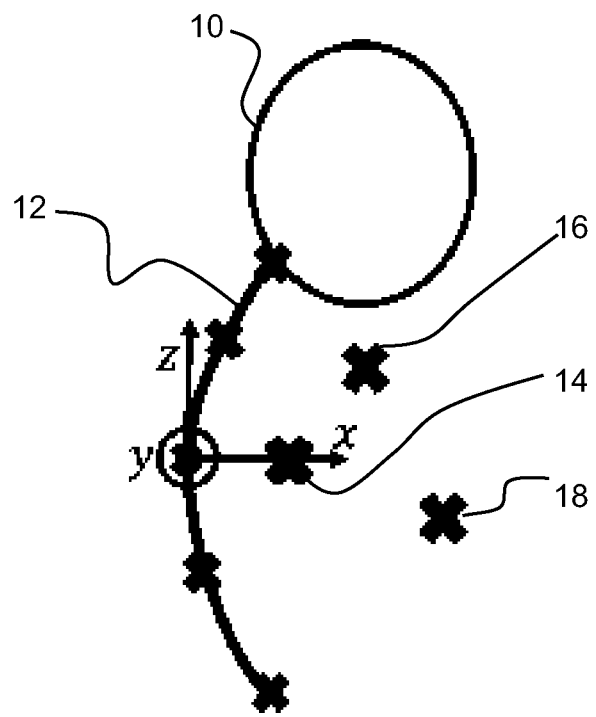
FIG. 1 shows a representation of a fetus with the xyz referential axes allocated to the fetus as proposed in the invention.

FIG. 1 shows a representation of a fetus comprising a head 10 and spine 12. The fetus is positioned within 3D space as defined by the axes x,y,z and with an origin at the center of the spine.

When selecting 2D ultrasound image planes from a 3D ultrasound scan, planes are selected to pass through landmarks of interest. These landmarks are typically organs or other anatomical features such as the stomach 14, heart 16 or umbilical insertion 18.

This invention relates to an alignment procedure by which an image is aligned in a consistent way in 3D space before further image analysis. The further image analysis may be for locating the landmarks so that desired imaging planes may be automatically generated, or it may be for populating a training database.

Thus. the method of the invention may be used for individual image analysis and/or for image analysis to populate a training database.

The first step in the method is to detect the spine and derive a first reference (orientation) axis.

The spine may be automatically detected in a 3D ultrasound image by combining a morphological filter which detects elongated bright structures and a deep learning (DL) based vertebrae detector, in order to take advantage of the strengths of both methods.

A morphological filter may be used. for each voxel x in the US volume in a given spherical neighborhood, to compare the intensity of the voxels along a direction u with the intensity of the other voxels. The filter responses are computed for various neighborhood radii and orientations u and combined to obtain a global response. The global responses of neighboring voxels are aggregated to define connected components which correspond to the best filter responses.

Although some of the responses are accurately positioned on the spine using this approach, others may also be present which are outliers, that may for example be located on ribs or other elongated structures such as long bones.

The deep learning-based vertebrae detector is a 2D fully convolutional network whose input is made of 2D slices, extracted orthogonally to the original identified z-axis. The volume slicing produces a large amount of data with similar features, which is appropriate for deep learning methods. The network output is a down sampled probability map, with values closer to 1 where the spine might be located. A 3D deep learning-based vertebrae detector is formed by stacking all the obtained 2D probability maps for one volume. This output heatmap is coarser than the morphological filter output, but more robustly located around the vertebrae.

By combining the deep-learning vertebrae detector and the morphological filter responses, the network output is refined and the filter responses that are outside the spine are rejected, so that a robust spine binary mask is finally obtained.

This is one way to identify the spine location, but any other suitable image processing techniques may be employed for detecting the unique spine shape.

Figure 2:
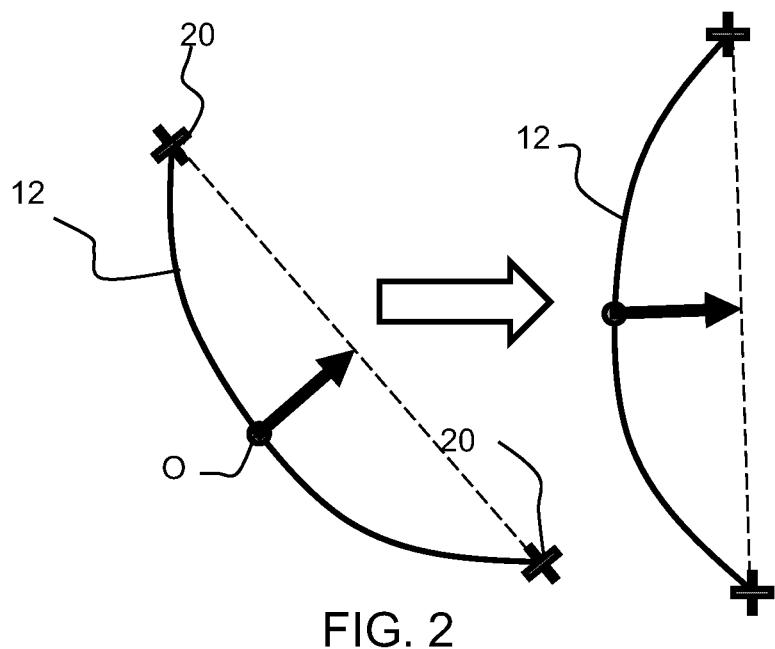
FIG. 2 shows a randomly oriented spine and a rotated version to a defined vertical orientation.

FIG. 2 shows on the left a randomly oriented spine 12. The spine detection basically involves identifying the spine, and using the center of mass of the spine binary mask to define the origin O of a reference coordinate system. If the detected spine is highly curved, its center of mass might not belong to the binary mask. This is because the so-called barycenter of the spine can be outside the spine itself and hence not aligned with the mask. In this case, the binary mask point that is the closest to the center of mass is used. Then the extremities 20 of the spine binary mask are used to define the vertical z axis. Alternatively a normal direction tangential to the central point of the spine may be used. The resulting z axis is shown in FIG. 1.

By defining the z axis, the image can be updated to include the z axis information, for example by rotating the image to position the z-axis in the defined (e.g. vertical) orientation, as shown in the right part of FIG. 2.

The second step in the method is to detect a second, orthogonal reference (orientation) axis. This is based on detection of the abdomen to define a transverse axis.

A set of planes are searched, each orthogonal to the first reference axis z (or locally orthogonal to the spine). Searching for an orientation axis is conducted in a set of xy planes, each passing through a local origin, with the local origins as evenly spaced points along the spine.

Figure 3:
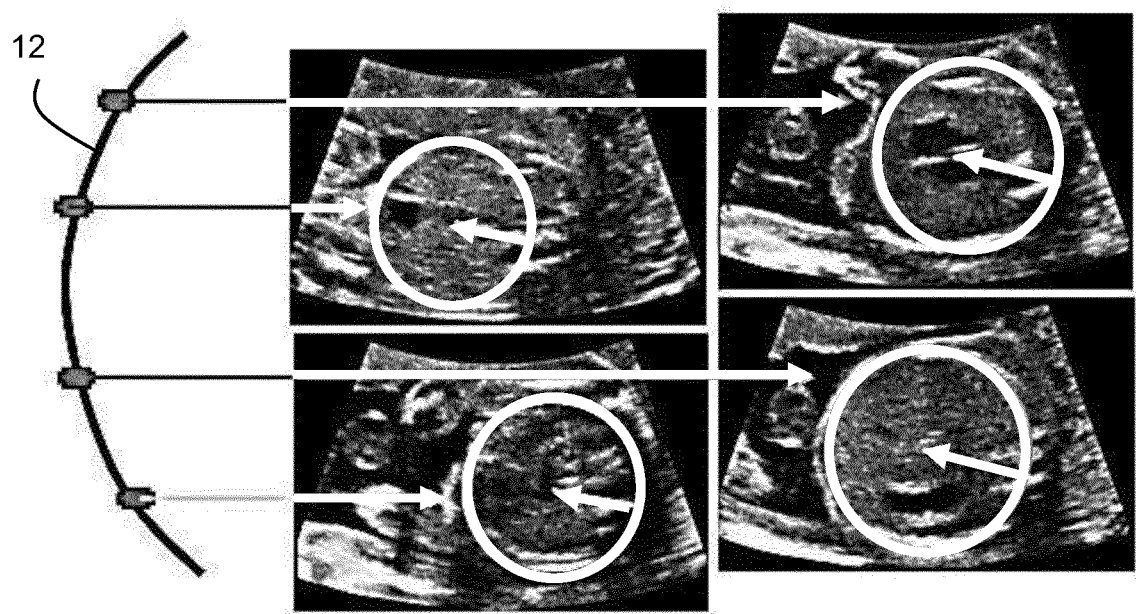
FIG. 3 shows the spine with four xy imaging planes spaced along the spine.

FIG. 3 shows the spine 12 with four xy imaging planes spaced along the spine. The images are shown to the right.

Within each of these 2D images, abdomen detection takes place, for example using a variant of the Hough transform, tailored to the detection of circular or elliptical shapes. In practice, the best convolution of the image with a radially-symmetric kernel modeling a disk with the desired border profile is searched among a range of radii.

A resulting located circle is shown in each image.

Figure 4:
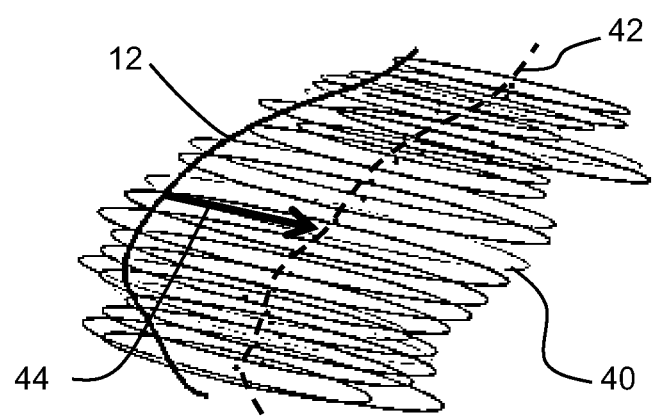
FIG. 4 shows the set of located circles or ellipses along the spine planes as well as their center points.

FIG. 4 shows the set of located circles or ellipses 40 along the spine planes as well as their center points 42. The convex hull the abdomen is defined.

For each plane, there is computation of the vector going from the spine intersection with the plane to the center of the detected circle. These vector arrows are shown in FIG. 3, and one such vector 44 is shown in FIG. 4.

The abdomen detection thus involves detecting an elliptical or circular form of the abdomen or thorax of the fetus in each plane, and identifying a vector within each plane which relates to the rotational orientation of the fetus in that plane.

All of these vectors are then projected onto the transverse plane through the central origin O. The x axis reference direction is then defined as an average projected vector in this reference xy plane. The resulting x axis is shown in FIG. 1 and it defines a second reference axis. From these two axes, the third coordinate axis, y, may be chosen to be orthogonal with right-handed orientation.

The average vector may comprise a weighted average, with greater weighting in the middle of the spine than at the ends of the spine.

Thus, by measuring two reference axes and then defining the third in a deterministic way, a normalized orientation in 3D space may be defined.

It is next desirable to identify the head-toe orientation of the volume and choose between the two possible directions of the z axis.

This may be achieved by training a classifier to distinguish between the two configurations in a 2D slice of the volume in the xz plane.

Figure 5:
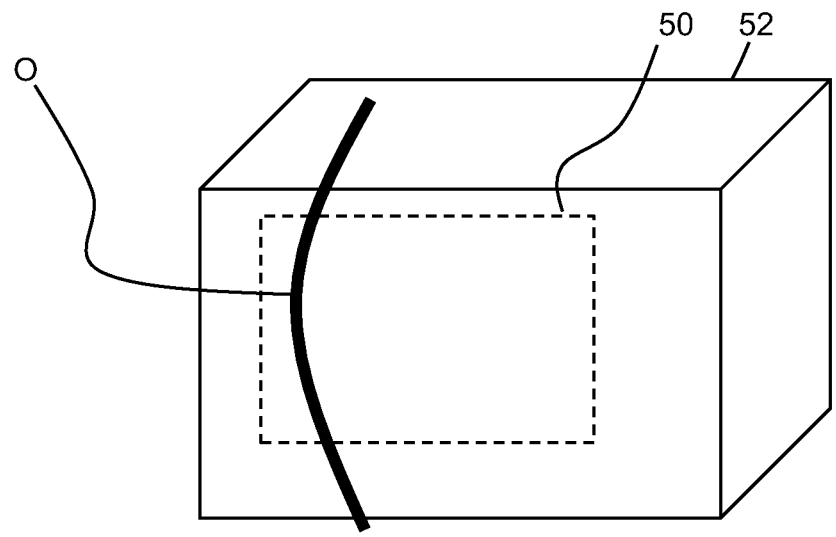
FIG. 5 shows an xz plane within the general volume.

FIG. 5 shows an xz plane 50 within the general volume 52 which passes through the origin O. This plane passes along the spine.

Figure 6:
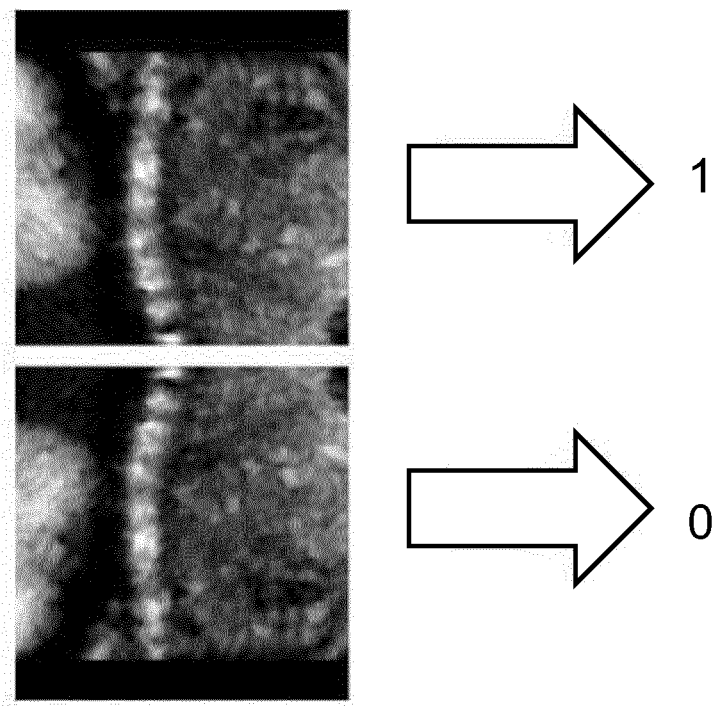
FIG. 6 shows two images in the xz plane with opposite orientation of the fetus.

FIG. 6 shows two images in the xz plane with opposite orientation of the fetus. Using image recognition approaches, the orientation can be identified based on previous machine learning from a testing set. A convolutional neural network may be used for this purpose.

For the machine learning step (to provide the reference for the image recognition), in order to be robust to possible inaccuracies during the spine detection step, random noise may be added during the xz slice extraction so that the network is fed with corrupted data during the training. Then, random patches are selected in the slice to train the classifier. The patch size may be selected based on gestational age and image resolution so that all structures have a normalized size. The output is binary 1 when the fetus head is at the top of the image, binary 0 if it is at the bottom.

The eventual detection of the orientation in use when analyzing a single image is implemented with a similar process, without the random noise addition.

The method steps explained above enable the fetal image to be mapped to a known orientation in 3D space.

To reduce scale variability due to varying gestational ages (GA), a scaling factor may also be applied to all volumes based on existing growth tables, for example before the orientation mapping.

For example the table below shows scaling factors for different gestational age ("GA") ranges (in weeks).

| | |
|---|---|
| GA_0_20 | 2.43 |
| GA_20_25 | 1.30 |
| GA_25_30 | 1.00 |
| GA_30_35 | 0.83 |
| GA_35_42 | 0.70 |

Figure 7:
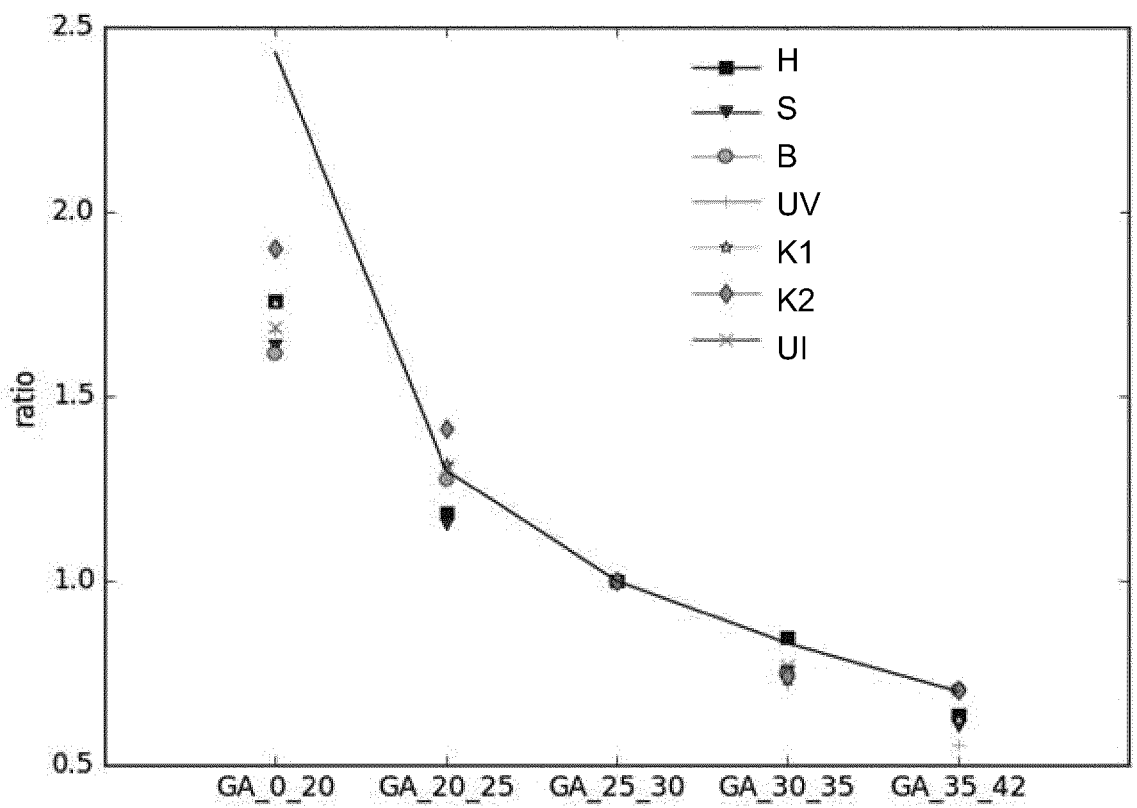
FIG. 7 shows a scaling function graphically.

FIG. 7 shows this scaling function graphically. The y-axis plots the scaling ratio, and the x-axis plots the gestational age ranges. The points show the distances to the origin for different anatomical features (H heart, S stomach, B bladder, UV umbilical vein, K1 kidney 1, K2 kidney 2, UI umbilical insertion).

For each volume, the distance between an organ, for example the Heart (H), and the origin O (as defined above) is measured. The examinations are grouped per GA range into the five groups shown. Within each group, the average distance for each organ is computed. The GA_25_30 group is used as a reference (hence the perfect alignment of all organs for the GA_25_30 group with the plot, with a ration value of 1) and each averaged distance in each group is divided by the values obtained in group GA_25_30. The results are plotted as the points in the graph. The continuous curve represents the theoretical ratios presented in the table above. The discrepancy between the measured values and the theoretical ratios results from the sample set used, and in particular the spread of samples within each GA range.

The method may also provide intensity normalization. Due to varying acquisition gains and imaging conditions, the relative intensity of various organs may vary significantly. Intensity normalization is desirable to assist the feature extraction in the machine learning approach. One approach is to use the mean and standard deviation, using a common normalization look up table.

Figure 8:
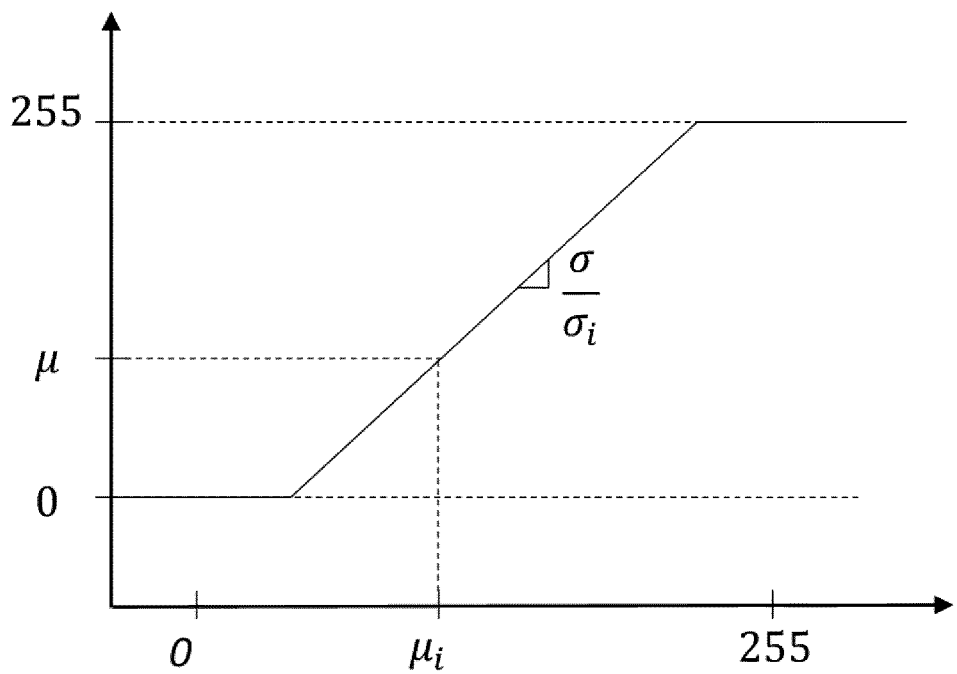
FIG. 8 is an illustration of an intensity normalization look-up-table.

FIG. 8 is an illustration of a database look-up-table to perform intensity normalization of ultrasound acquisitions. The x-axis shows the intensity range for a particular image, with mean intensity $\mu_i$ and standard deviation $\sigma_i$ of the pixel intensity values. The database provides an intensity mapping so that each image is transformed to have a reference standard deviation $\sigma$ and a reference mean $\mu$. The reference intensity characteristics are shown by the y-axis.

Thus, the 3D image volumes are rotated, translated, intensity scaled, and size scaled so that the associated fetus landmarks are perfectly aligned with respect to a common reference.

The method above may be used to process a single captured 3D ultrasound image or to create the training database (as already mentioned above). These two uses of the method will now be explained.

Figure 9:
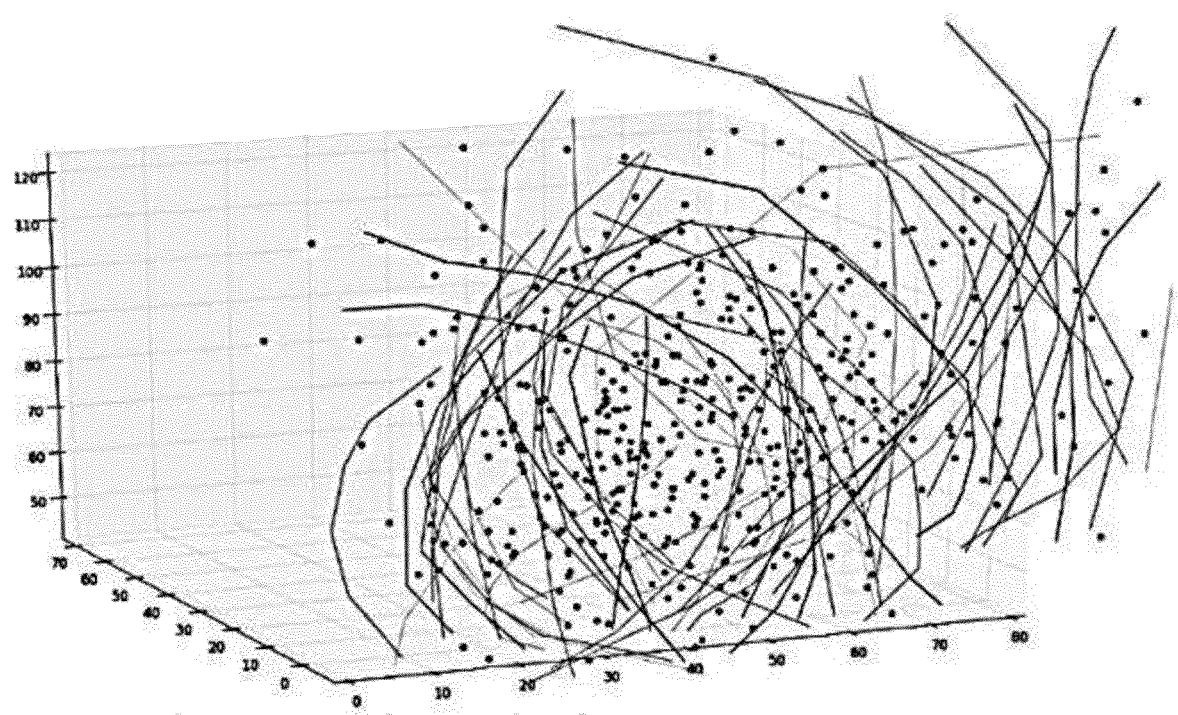
FIG. 9 shows a large set of 3D US abdominal acquisitions with lines to show the identified spine orientations and dots as the locations of landmarks.

FIG. 9 shows a large set of 3D US abdominal acquisitions. The lines show the identified spine orientations. Each image is annotated by a clinician to identify the locations of landmarks such as the heart and stomach, and these are shown as dots. These landmarks annotated images are used to create the training database which implements machine learning.

FIG. 9 shows the high variability of fetus positions and orientations and confirms that learning on such a database will include variability due to spatial positioning instead of focusing on real anatomical variations.

Figure 10:
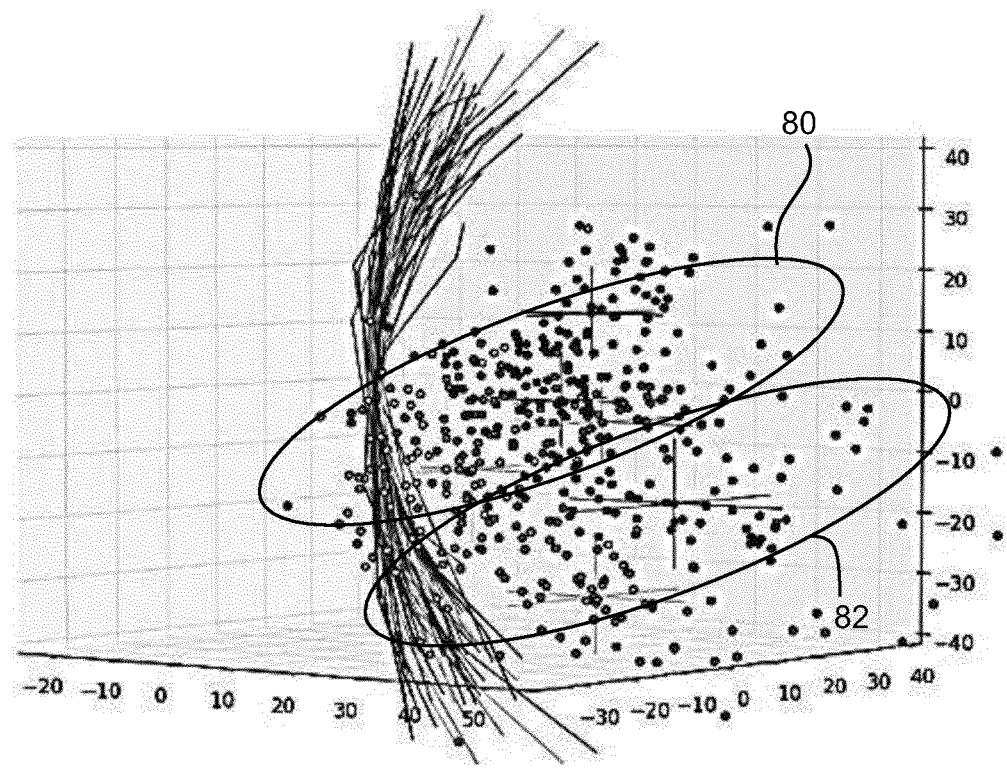
FIG. 10 shows the 3D US abdominal acquisitions after re-orientation and scaling.

The 3D orientation (and scaling) process explained above gives rise to the images shown in FIG. 10. The heart locations are generally approximately in the area 80 and the stomach locations are generally approximately in the area 82.

These aligned images are instead used for a learning-based approach, which then enables more robust detection of the fetus landmark positions.

The training database uses machine learning based on the annotated images in order to learn landmark (e.g. organ) positions. The machine learning may be based on a random forest algorithm (for example disclosed in Criminisi, A., J., S., Konukoglu, E.: Decision forests: A unified framework for classification, regression, density estimation, manifold learning and semi-supervised learning. Foundations and Trends in Computer Graphics and Vision (2012). An approach may be used as disclosed in Cuingnet, R., Prevost, R., Lesage, D., Cohen, L. D., Mory, B., Ardon, R.: Automatic Detection and Segmentation of Kidneys in 3D CT Images using Random Forests. In: Proceedings of MIC-CAI'12. vol. 7512, pp. 66-74 (2012).

The principle is to learn, for a given point in a volume, the relative direction to the target landmarks. In the following description, such a relative direction is referred to as a voting vector.

In order to train the random forest algorithm, it is necessary to set the values of a number of parameters. The most influential ones are the following: number of trees NT, depth of trees DT, number of training points NP per image, and threshold α on variance of voting vectors in a node. The algorithm also depends on image-based features (f). The features are for example mostly derived from local gradients, such as locally normalized gradients and distances to gradients.

A splitting criterion is defined for all nodes. It aims at finding two subsets of training points so that the sum of the entropy of both subsets is minimal. The splitting criterion is obtained by testing a large set of random features at each node. Within this set, the feature that provides the optimal subset separation is selected together with the corresponding splitting threshold (θ) and stored in the node. The entropy criterion is defined as the variance of the voting vectors to each landmark.

Multiple stopping criteria are defined for all leaves: (i) when a given depth DT of the tree is reached, (ii) when the intra-subset variance is below a given threshold α, (iii) when the subset is too small. The mean of the voting vectors is stored in each leaf. This will be the voting vector of each point classified in this leaf.

This is just one generic description of how machine learning may be used to train a database for identification of landmarks, having positions relative to an identified structure. Of course, other pattern recognition approaches may be used.

The purpose of the training database is to enable automated identification of landmarks in a non-annotated 3D image volume.

For this purpose, a scanned image is subjected to the same orientation, scaling and intensity normalization as explained above.

The actual landmark localization process is restricted to the volume area located inside the abdomen convex hull. For a given input volume, the following steps are performed:

P random testing points are selected;

the testing points are propagated throughout the tree, using the (f, θ) splitting and feature criteria, until they reach a leaf;

each point provides a voting vector; and all voting vectors are converted into landmark predictions.

To provide a single prediction, all predictions are combined through Gaussian estimation to convert a set of all predictions into a single extracted prediction.

When landmarks have been identified, they may be used for the automatic extraction of clinical planes. Each clinical plane may be defined by three landmarks.

Figure 11:
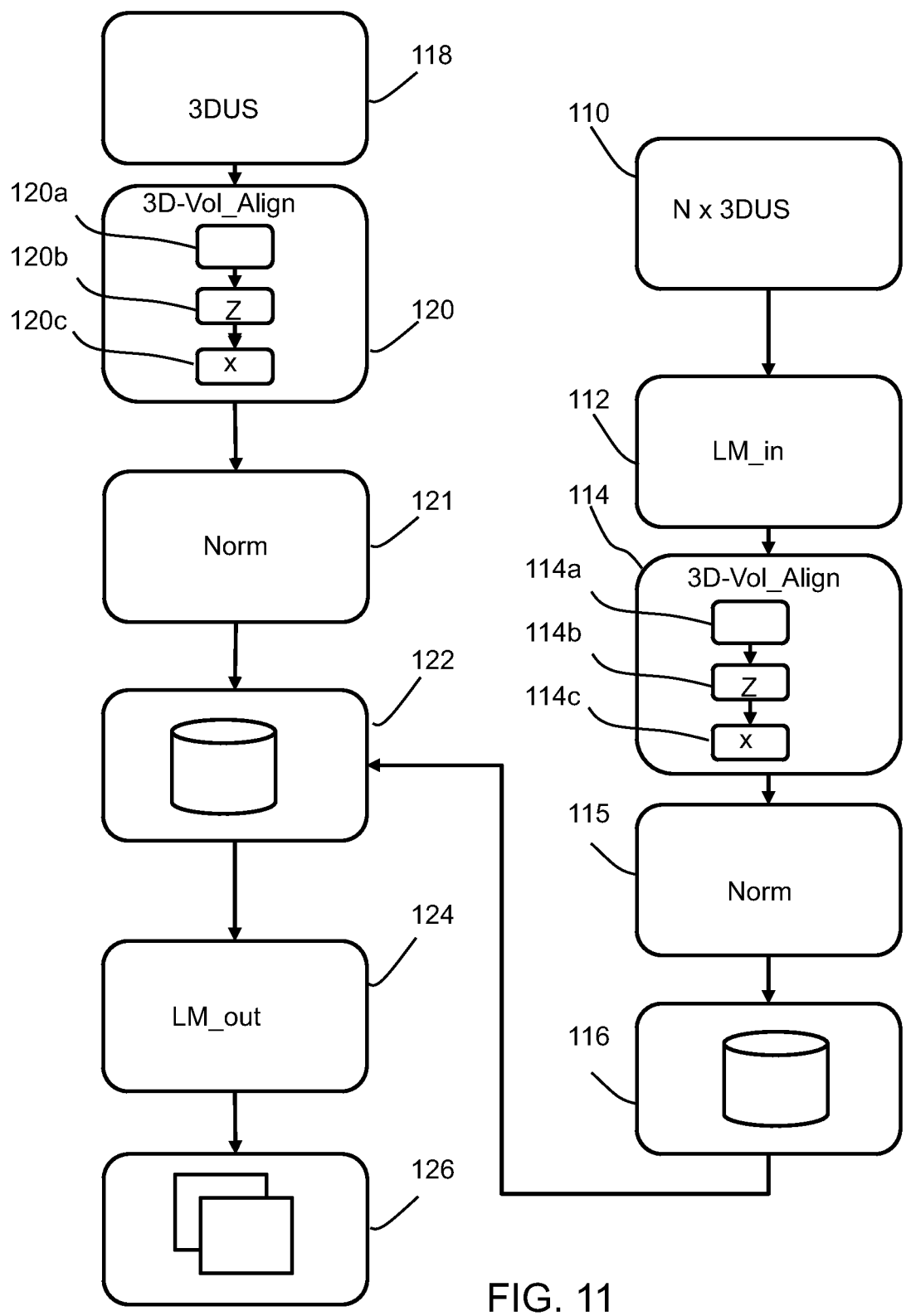
FIG. 11 shows methods in accordance with the invention.

FIG. 11 shows methods in accordance with the invention.

The right side shows a method of generating the training database. It comprises:

in step 110 receiving a training set of N 3D fetal ultrasound images. These include annotations from clinicians. Thus, in step 112, identification of landmarks within each 3D fetal ultrasound image of the training set is received.

In step 114, each 3D fetal ultrasound image of the training set is processed using the method as described above, to provide at least 3D re-orientation.

This involves detecting the spine within the image in step 114a, determining the first reference axis (z) based on the spine (12) orientation and location within the image in step 114b. In step 114c, the second reference axis (x) is determined, perpendicular to the first reference axis (z), based on the fetal torso orientation with respect to the detected spine.

Preferably also intensity normalization and scaling is carried out in normalization step 115. This processing results in orientation of each 3D fetal ultrasound image of the training set using the respective first and second reference axes.

In step 116 machine learning is applied to the oriented training set to provide an algorithm which can determine the location of landmarks for a 3D fetal ultrasound image without corresponding identification of landmarks.

As explained above, when generating the training database, a particular method is used for determining the head/toe orientation of the fetus (during the step 114). The plane of interest defined by the first and second reference axes is extracted, in particular the xz plane, and patches of a determined patch size are randomly sampled. A classifier is then based on the patches, wherein the classifier indicates the head/toe orientation of the fetus.

The left side of FIG. 11 shows the method of identifying landmarks within a new (meaning not included in the training database) 3D fetal ultrasound image.

The method comprises in step 118 receiving a 3D fetal ultrasound image. This may be in real time, but equally the method may be applied to a stored image.

In step 120, the 3D fetal ultrasound image is re-oriented and then preferably rescaled and intensity normalized in step 121, using the method as described above. There are again steps of detecting the spine 120a, determining the first reference axis (z) 120b and determining the second reference axis (x) in step 120c. The 3D fetal ultrasound image is re-oriented using the first and second reference axes generated by the method described above.

In step 122 the re-oriented 3D fetal ultrasound image is analyzed using the machine learning algorithm derived from the training database (from step 116) which comprises landmark information thereby to locate corresponding landmark information for the 3D fetal ultrasound image.

Optionally, the landmark positions are output in step 124.

In step 126, the landmark positions are used to automatically define image slices to be generated from the 3D ultrasound volume.

The invention is for use for processing 3D fetal ultrasound images using a diagnostic imaging system.

Figure 12:
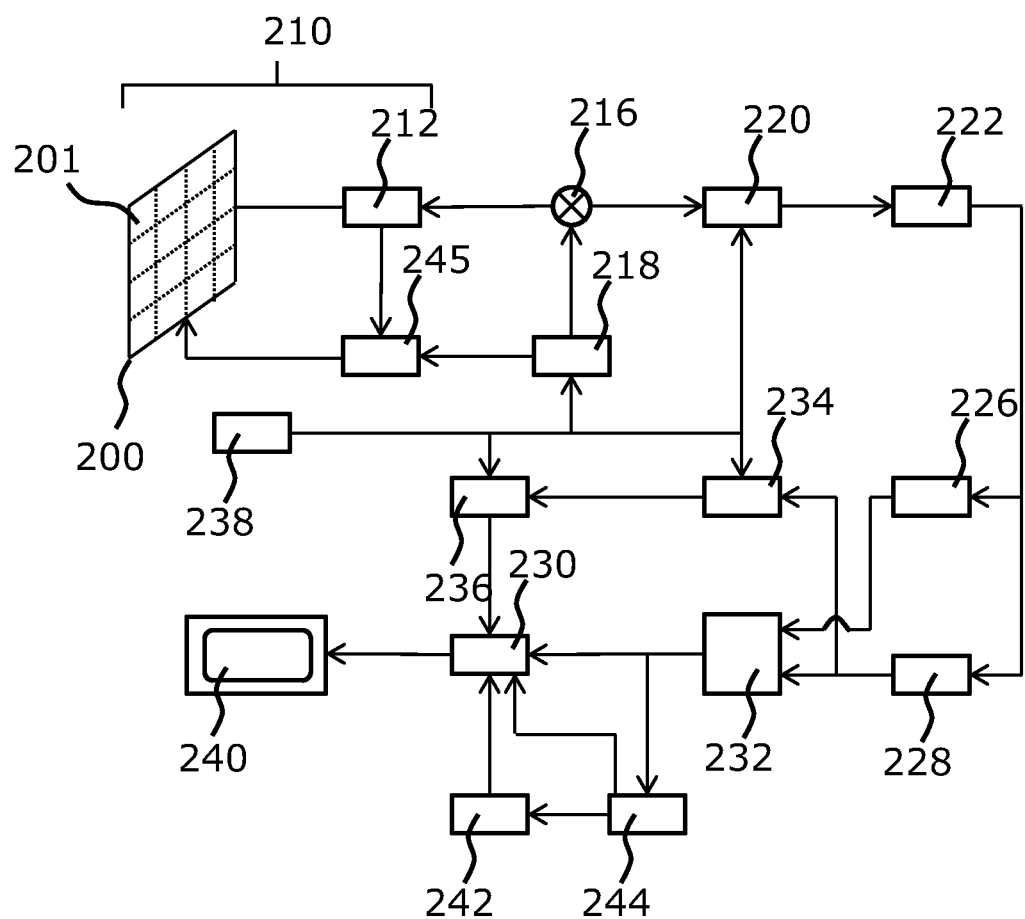
FIG. 12 shows an exemplary ultrasound diagnostic imaging system.

For completeness, the general operation of an exemplary ultrasound diagnostic imaging system will first be described, with reference to FIG. 12, and with emphasis on the signal processing function of the system since this invention relates to the processing of the signals measured by the transducer array.

The system comprises an array transducer probe 210 which has a CMUT transducer array 200 for transmitting ultrasound waves and receiving echo information. The transducer array 200 may alternatively comprise piezoelectric transducers formed of materials such as PZT or PVDF. The transducer array 200 is a two-dimensional array of transducers 201 capable of scanning in three dimensions for 3D imaging.

The transducer array 200 is coupled to a microbeamformer 212 in the probe which controls reception of signals by the CMUT array cells or piezoelectric elements. Microbeamformers are capable of at least partial beamforming of the signals received by sub-arrays (or "groups" or "patches")

of transducers as described in U.S. Pat. No. 5,997,479 (Savord et al.), U.S. Pat. No. 6,013,032 (Savord), and U.S. Pat. No. 6,623,432 (Powers et al.).

Note that the microbeamformer is entirely optional. The examples below assume no analog beamforming.

The microbeamformer 212 is coupled by the probe cable to a transmit/receive (T/R) switch 216 which switches between transmission and reception and protects the main beamformer 220 from high energy transmit signals when a microbeamformer is not used and the transducer array is operated directly by the main system beamformer. The transmission of ultrasound beams from the transducer array 210 is directed by a transducer controller 218 coupled to the microbeamformer by the T/R switch 216 and a main transmission beamformer (not shown), which receives input from the user's operation of the user interface or control panel 238.

One of the functions controlled by the transducer controller 218 is the direction in which beams are steered and focused. Beams may be steered straight ahead from (orthogonal to) the transducer array, or at different angles for a wider field of view. The transducer controller 218 can be coupled to control a DC bias control 245 for the CMUT array. The DC bias control 245 sets DC bias voltage(s) that are applied to the CMUT cells.

In the reception channel, partially beamformed signals are produced by the microbeamformer 212 and are coupled to a main receive beamformer 220 where the partially beamformed signals from individual patches of transducers are combined into a fully beamformed signal. For example, the main beamformer 220 may have 128 channels, each of which receives a partially beamformed signal from a patch of dozens or hundreds of CMUT transducer cells or piezoelectric elements. In this way the signals received by thousands of transducers of a transducer array can contribute efficiently to a single beamformed signal.

The beamformed reception signals are coupled to a signal processor 222. The signal processor 222 can process the received echo signals in various ways, such as band-pass filtering, decimation, I and Q component separation, and harmonic signal separation which acts to separate linear and nonlinear signals so as to enable the identification of nonlinear (higher harmonics of the fundamental frequency) echo signals returned from tissue and micro-bubbles. The signal processor may also perform additional signal enhancement such as speckle reduction, signal compounding, and noise elimination. The band-pass filter in the signal processor can be a tracking filter, with its pass band sliding from a higher frequency band to a lower frequency band as echo signals are received from increasing depths, thereby rejecting the noise at higher frequencies from greater depths where these frequencies are devoid of anatomical information.

The beamformers for transmission and for reception are implemented in different hardware and can have different functions. Of course, the receiver beamformer is designed to take into account the characteristics of the transmission beamformer. In FIG. 12 only the receiver beamformers 212, 220 are shown, for simplicity. In the complete system, there will also be a transmission chain with a transmission micro beamformer, and a main transmission beamformer.

The function of the micro beamformer 212 is to provide an initial combination of signals in order to decrease the number of analog signal paths. This is typically performed in the analog domain.

The final beamforming is done in the main beamformer 220 and is typically after digitization.

The transmission and reception channels use the same transducer array 210 which has a fixed frequency band. However, the bandwidth that the transmission pulses occupy can vary depending on the transmission beamforming that has been used. The reception channel can capture the whole transducer bandwidth (which is the classic approach) or by using bandpass processing it can extract only the bandwidth that contains the useful information (e.g. the harmonics of the main harmonic).

The processed signals are coupled to a B mode (i.e. brightness mode, or 2D imaging mode) processor 226 and a Doppler processor 228. The B mode processor 226 employs detection of an amplitude of the received ultrasound signal for the imaging of structures in the body such as the tissue of organs and vessels in the body. B mode images of structure of the body may be formed in either the harmonic image mode or the fundamental image mode or a combination of both as described in U.S. Pat. No. 6,283,919 (Roundhill et al.) and U.S. Pat. No. 6,458,083 (Jago et al.) The Doppler processor 228 processes temporally distinct signals from tissue movement and blood flow for the detection of the motion of substances such as the flow of blood cells in the image field. The Doppler processor 228 typically includes a wall filter with parameters which may be set to pass and/or reject echoes returned from selected types of materials in the body.

The structural and motion signals produced by the B mode and Doppler processors are coupled to a scan converter 232 and a multi-planar reformatter 244. The scan converter 232 arranges the echo signals in the spatial relationship from which they were received in a desired image format. For instance, the scan converter may arrange the echo signal into a two dimensional (2D) sector-shaped format, or a pyramidal three dimensional (3D) image. The scan converter can overlay a B mode structural image with colors corresponding to motion at points in the image field with their Doppler-estimated velocities to produce a color Doppler image which depicts the motion of tissue and blood flow in the image field. The multi-planar reformatter will convert echoes which are received from points in a common plane in a volumetric region of the body into an ultrasound image of that plane, as described in U.S. Pat. No. 6,443,896 (Detmer). A volume renderer 242 converts the echo signals of a 3D data set into a projected 3D image as viewed from a given reference point as described in U.S. Pat. No. 6,530,885 (Entrekin et al.).

The 2D or 3D images are coupled from the scan converter 232, multi-planar reformatter 244, and volume renderer 242 to an image processor 230 for further enhancement, buffering and temporary storage for display on an image display 240. In addition to being used for imaging, the blood flow values produced by the Doppler processor 28 and tissue structure information produced by the B mode processor 226 are coupled to a quantification processor 234. The quantification processor produces measures of different flow conditions such as the volume rate of blood flow as well as structural measurements such as the sizes of organs and gestational age. The quantification processor may receive input from the user control panel 238, such as the point in the anatomy of an image where a measurement is to be made. Output data from the quantification processor is coupled to a graphics processor 236 for the reproduction of measurement graphics and values with the image on the display 240, and for audio output from the display device 240. The graphics processor 236 can also generate graphic overlays for display with the ultrasound images. These graphic overlays can contain standard identifying information such as patient name, date and time of the image, imaging parameters, and the like. For these purposes the graphics processor receives input from the user interface 238, such as patient name. The user interface is also coupled to the transmit controller 218 to control the generation of ultrasound signals from the transducer array 210 and hence the images produced by the transducer array and the ultrasound system. The transmit control function of the controller 218 is only one of the functions performed. The controller 218 also takes account of the mode of operation (given by the user) and the corresponding required transmitter configuration and band-pass configuration in the receiver analog to digital converter. The controller 218 can be a state machine with fixed states.

The user interface is also coupled to the multi-planar reformatter 244 for selection and control of the planes of multiple multi-planar reformatted (MPR) images which may be used to perform quantified measures in the image field of the MPR images.

The image processing functions described above may for example be performed by the image processor 230.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measures cannot be used to advantage. Any reference signs in the claims should not be construed as limiting the scope.

The invention claimed is:

1. A computer implemented method for processing a 3D fetal ultrasound image, the method comprising:
    obtaining a 3D fetal ultrasound image;
    detecting the spine within the image;
    determining a first reference axis based on the spine orientation and location within the image;
    determining a second reference axis, perpendicular to the first reference axis, based on the fetal torso orientation with respect to the detected spine; and
    updating the 3D fetal ultrasound image using the first and second reference axes;
    wherein the determining of the second reference axis comprises:
    extracting a set of planes, each orthogonal to the first reference axis or locally orthogonal to the spine;
    detecting an elliptical or circular form of the abdomen or thorax of the fetus in each plane; and
    determining the second reference axis based on an orientation vector in each plane between the spine and the center of the elliptical form.

2. A method as claimed in claim 1, wherein the elliptical form is obtained by performing a Hankel transform on the plane.

3. A method as claimed in claim 1, wherein the generating of the second reference axis comprises:
    projecting the orientation vectors on a central plane located at the middle of the spine;
    taking an average of the projected orientation vectors; and
    using the average of the projected orientation vectors to form the second reference axis.

4. A method as claimed in claim 3, wherein taking an average comprises calculating a weighted average, with greater weighting in the middle of the spine than at the ends of the spine.

5. A method as claimed in claim 1, wherein the method further comprises:
    determining a head/toe orientation of the 3D fetal ultrasound image; and
    updating the 3D fetal ultrasound image using the head/toe orientation.

6. A method as claimed in claim 1, wherein the method further comprises:
    performing intensity normalization on the 3D fetal ultrasound image; and/or
    scaling the 3D fetal ultrasound image based on a fetal gestation age.

7. A method as claimed in claim 1, wherein the detecting of the spine within the 3D fetal ultrasound image comprises:
    analyzing the image with a morphological filter adapted to detect elongated bright structures;
    analyzing the image with a deep learning-based vertebrae detector; and
    obtaining a spine mask based on the responses from the morphological filter and from the deep learning-based vertebrae detector.

8. A method of identifying landmarks within a 3D fetal ultrasound image, comprising:
    receiving a 3D fetal ultrasound image;
    processing the 3D fetal ultrasound image using the method as claimed in claim 1;
    orienting the 3D fetal ultrasound image using the first and second reference axes; and
    analyzing the oriented 3D fetal ultrasound image with a machine learning algorithm derived from a training database which comprises landmark information, thereby to locate corresponding landmark information for the 3D fetal ultrasound image.

9. A method of generating a training database based on 3D fetal ultrasound images and generating an algorithm, comprising:
    receiving a training set of 3D fetal ultrasound images;
    receiving identification of landmarks within each 3D fetal ultrasound image of the training set;
    processing each 3D fetal ultrasound image of the training set using the method as claimed in claim 1;
    orienting each 3D fetal ultrasound image of the training set using the respective first and second reference axes and head/toe orientation; and
    using machine learning to the oriented training set to provide an algorithm which can determine the location of landmarks for a 3D fetal ultrasound image without corresponding identification of landmarks.

10. A method as claimed in claim 9, comprising determining the head/toe orientation of the fetus during the processing of each 3D fetal ultrasound images by:
    extracting a plane of interest defined by the first and second reference axes;
    randomly sampling patches, of a determined patch size, of the extracted plane of interest; and
    generating a classifier based on the patches, wherein the classifier indicates the head/toe orientation of the fetus.

11. A method as claimed in claim 10, wherein the patch size is based on a fetal gestation age and a resolution of the 3D fetal ultrasound image.

12. A method as claimed in claim 8, wherein the machine learning algorithm is generated.

13. A controller for controlling the processing a 3D fetal ultrasound image, the controller comprising instructions thereon that when executed cause the controller to implement the method of claim 1.

14. An ultrasound system, the system comprising:
an ultrasonic probe, the ultrasonic probe comprising an array of transducer elements, wherein the ultrasonic probe is adapted to obtain a 3D fetal ultrasound image of a region of interest;
a controller as claimed in claim 13; and
a display device for displaying the aligned 3D fetal ultrasound image,
wherein the controller is adapted to analyze the updated 3D fetal ultrasound image using a machine learning algorithm derived from a training database, thereby to derive landmark locations within the 3D fetal ultrasound image.

\* \* \* \* \*